United States Patent [19]

Korb et al.

[11] Patent Number: 5,475,107
[45] Date of Patent: Dec. 12, 1995

[54] PROCESS FOR OBTAINING 3,7-DIALKYLXANTHINES FROM 3-ALKYL-XANTHINES

[75] Inventors: Gerhard Korb, Hainburg; Hans-Wolfram Flemming, Usingen, both of Germany

[73] Assignee: Hoechst-Roussel Pharmaceuticals Incorporated, Somerville, N.J.

[21] Appl. No.: 149,488

[22] Filed: Nov. 9, 1993

[30] Foreign Application Priority Data

Nov. 10, 1992 [DE] Germany ............... 42 37 814.1

[51] Int. Cl.$^6$ .............. C07D 473/10; C07D 473/06
[52] U.S. Cl. ............ 544/273; 544/271; 544/272
[58] Field of Search ............................ 544/273

[56] References Cited

U.S. PATENT DOCUMENTS

| | | | |
|---|---|---|---|
| 3,737,433 | 6/1973 | Mohler et al. | 544/271 |
| 4,450,163 | 5/1984 | Philippossian | 544/273 |
| 4,544,556 | 10/1985 | Fedi | 544/273 |

FOREIGN PATENT DOCUMENTS

| | | |
|---|---|---|
| 267796 | 7/1990 | Czechoslovakia . |
| 267100 | 12/1990 | Czechoslovakia . |
| 019165 | 11/1980 | European Pat. Off. . |
| 319854 | 12/1988 | European Pat. Off. . |
| 864869 | 7/1949 | Germany . |
| 222026 | 5/1985 | Germany . |
| 3741883 | 6/1989 | Germany . |

OTHER PUBLICATIONS

Searcey, Syn. Comm 19, 1309 (1989).
Ullmanns Encyklopadie der technischen Chemie, Band 19, Polyacyl–Verbindungen bis Quecksilber, pp. 579–580. A translation is not readily available. (1978).
Derwent 93–025154 (Nro 101,894) (1991).
Chem. Abstracts 113:40721u; (Rybar et al I, 1989).
Chem. Abstracts 115:279704u; (Rybar et al III, 1990).
Chem. Abstracts 113:40720t; (Rybar et al II, 1989).
Chem. Abstracts 114:185144p; (Rybar et al IV, 1990).
Chem Abs. 117, 90053f (Ryber et al V, 1991).

*Primary Examiner*—Mark L. Berch
*Attorney, Agent, or Firm*—Barbara V. Maurer

[57] ABSTRACT

Process for obtaining 3,7-dialkylxanthines from 3-alkyl-xanthines 3,7-Dialkylxanthines are obtained from the corresponding 3-alkylxanthines using an alkylating agent in the presence of quaternary ammonium and/or phosphonium compounds and, where appropriate, of additional polyethers in a two-phase mixture.

16 Claims, No Drawings

PROCESS FOR OBTAINING 3,7-DIALKYLXANTHINES FROM 3-ALKYL-XANTHINES

DESCRIPTION

Process for obtaining 3,7-dialkylxanthines from 3-alkyl-xanthines 3,7-Dialkylxanthines are compounds of the formula I.

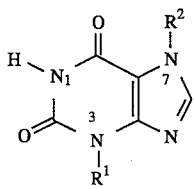

The unsubstituted 3,7-dialkylxanthines, or those substituted at position 1, are important precursors or intermediates in the preparation of pharmaceuticals. Thus, the compound 3,7-dimethylxanthine (theobromine) may, for example, be used as a precursor in the preparation of the active pharmaceutical constituent pentoxifylline (U.S. Pat. No. 3,737,433) of the formula VIII

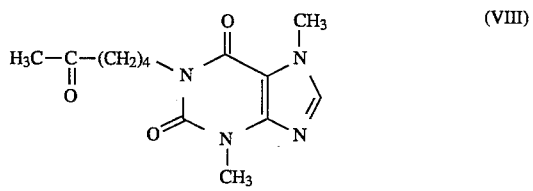

and of similar compounds which possess vasotherapeutic properties.

To obtain pentoxifylline (VIII) which fulfills the specification, theobromine must be employed in sufficiently high purity. Interfering effects are produced in particular by the starting compound 3-methylxanthine (II, $R^1=CH_3$), the overmethylated compound caffeine (IX) and the isomeric compound theophylline (X)

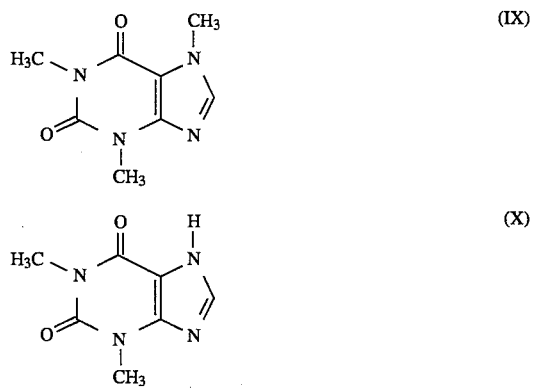

as well as coloring impurities.

Processes for preparing the compounds of the formula (I) are known in the literature. In these processes the main alkylating agents employed are dimethyl sulfate, dimethyl carbonate and methyl chloride, ethyl chloride, propyl chloride, diethyl sulfate, dipropyl sulfate, diethyl carbonate or dipropyl carbonate.

The processes using dimethyl sulfate as the methylating agent for preparing theobromine from 3-methylxanthine are summarised in the patent DD 222 026. Depending on the methylation method employed, theobromine is obtained in yields of 65 to 76% of theory, based on pure theobromine. However, in the processes with high theobromine yields, relatively large quantities of byproducts still usually arise, which byproducts, because of the quality requirements for the preparation of active pharmaceutical constituents, must be removed by an additional purification procedure.

The process using dimethyl carbonate as the methylating agent (DE 3 741 883) is a high pressure process which can only be carried out in special autoclaves which withstand pressures of 80 to 160 bar. In this process, the yields obtained are between 65.8 and 73.2% of theory of pure theobromine with a content of at least 99.6%, determined by HPLC.

The process using methyl chloride as the methylating agent for preparing theobromine (CS 267 100) in an aqueous or aqueous/alcoholic medium shows high yields. However, in this case, the theobromine must be very heavily contaminated with byproducts, since the reported melting points are very far removed from the melting point of pure theobromine. For example, a mixture of pure theobromine and about 5% of 3-methylxanthine still shows a melting point which is about 100° C. higher than that of theobromine prepared according to CS 267 100. It must therefore be assumed that considerable quantities of caffeine (IX) and possibly theophylline (X), which must be removed by purification, are still present in the isolated product. The loss of yield in the additional working up necessary to obtain pure theobromine is likely to be quite substantial.

Additionally, a process for preparing 3-methyl-7-propylxanthine (CS 267 796) is known, and the process is said to be improved by addition of small quantities of catalysts for interphase transfer, such as tetraalkylammonium salts or dimethylbenzylalkylammonium salts with 8 to 18 carbon atoms. However, the examples show that the addition of about 0.26 mmol of dimethylbenzylalkyl-ammonium bromide decreases the yield by 5% while the melting points of the products prepared with or without catalyst are the same.

In addition, the examples presented in Patent CS 267 100 show that the yield is smaller with larger batches. This fact has also been described in Patent DD 222 026. Our own experiments, in which the batch size was increased one hundredfold, show a clear diminution in the yield under the conditions described in CS 267 796.

It is the object of the present invention to find a process by which 3,7-dialkylxanthines may be selectively prepared from 3-alkylxanthines in high yields and with very high purities and very good space/time yields.

The invention therefore relates to a process for obtaining 3,7-dialkylxanthines of the formula I

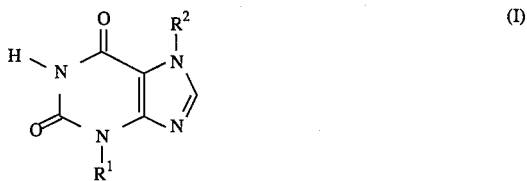

where $R^1$ and $R^2$, independently of each other, are $(C_1-C_6)$-alkyl, which may be straight-chain or branched, wherein a 3-alkylxanthine of the formula II

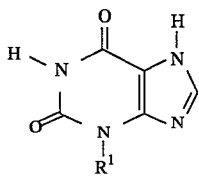

in which $R^1$ is $(C_1-C_6)$-alkyl, which may be straight-chain or branched, a) is converted in aqueous phase and using a basic agent into its salt and b) this salt is reacted in a two-phase mixture with an alkylating agent with 1 to 6 carbon atoms in the presence of at least one quaternary ammonium compound and/or phosphonium compound of the formulae III and IV

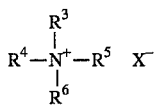

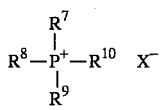

where $R^3$ to $R^{10}$ are identical or different and, independently of each other, are a) $(C_1-C_{20})$-alkyl, which may be straight-chain or branched, b) benzyl or c) phenyl and X is an anion, and c) where appropriate the alkylation is carried out in the presence of a linear polyether of the formula V $$R^{11}-O-(Y)_n-R^{12} \quad (V)$$

where $R^{11}$ and $R^{12}$ are identical or different and, independently of each other, are $(C_1-C_8)$-alkyl, Y is a radical from the group a) —CH$_2$—CH$_2$—O— or b) —CH$_2$—CH$_2$—CH$_2$—O— and n is an integer from 1 to 8.

In the process according to the invention, 3,7-dialkylxanthines of the formula I are preferably prepared in which $R^1$ and $R^2$, independently of each other, are $(C_1-C_3)$-alkyl.

3,7-Dialkylxanthines which are particularly preferred for the process are 3,7-dimethylxanthine (=compound of the formula I with $R^1=R^2=$—CH$_3$)

3-ethyl-7-propylxanthine (=compound of the formula I with $R^1$=—CH$_2$—CH$_3$ and $R^2$=CH$_2$—CH$_2$—CH$_3$)

3-methyl-7-propylxanthine (=compound of the formula I with $R^1$=CH$_3$ and $R^2$=—CH$_2$—CH$_2$—CH$_3$).

It is advantageous that there is a surprisingly high selectivity for alkylation in the 7 position on the xanthine, while alkylation at the 1 position hardly occurs. In addition, the compounds of the formulae III and/or IV, as well as of the formula V, where appropriate, may be readily separated from the aqueous phase and used for further reactions.

Alkali metal hydroxides and/or alkali metal carbonates, such as, for example, sodium hydroxide, potassium hydroxide, sodium hydrogen carbonate, potassium hydrogen carbonate, sodium carbonate or potassium carbonate are preferred basic agents.

The quaternary ammonium or phosphonium compounds of the formulae III and IV which are employed are advantageously those which are either insoluble or only sparingly soluble in water. Methyltrioctylammonium chloride, methyltrioctylammonium hydroxide, methyltricaprylammonium chloride, methyltricaprylammonium hydroxide, ethyltrioctylammonium chloride, ethyltrioctylphosphonium chloride and hexadecyltributylphosphonium bromide are preferred quaternary ammonium or phosphonium compounds of the formulae III and IV.

Ethylene glycol dibutyl ether, diethylene glycol dibutyl ether, triethylene glycol dibutyl ether, tetraethylene glycol dibutyl ether, diethylene glycol ethyl tert-butyl ether, propylene glycol dibutyl ether, dipropylene glycol dibutyl ether, polyethylene glycol dibutyl ether and polypropylene glycol dibutyl ether of different ether chain lengths (where n in the formula V is 2 to 8) are preferred polyethers of the formula V.

Preferred alkylating agents are $(C_1-C_6)$-alkyl halides such as alkyl chloride, alkyl bromide, alkyl fluoride or alkyl iodide, in particular methyl chloride, ethyl chloride or propyl chloride; $(C_1-C_6)$-dialkyl sulfates such as dimethyl, diethyl, dipropyl, dibutyl, dipentyl or dihexyl sulfate; or $(C_1-C_6)$-dialkyl carbonates such as dimethyl, diethyl, dipropyl, dibutyl, dipentyl or dihexyl carbonate.

The term anion is understood to mean chloride, bromide, hydrogen sulfate or hydroxide. The term alkyl is understood to mean hydrocarbon radicals such as methyl, ethyl, propyl, butyl, pentyl or hexyl. 3-$(C_1-C_6)$-alkylxanthines as starting substances for the alkylation reaction according to the invention can be prepared by processes known from the literature, for example by a modified "Traube synthesis" (Ullmanns Enzyklopädie der Technischen Chemie [Ullmann's Encyclopedia of Industrial Chemistry], 4th Edition, Volume 19 (1980) page 579).

In process step a) the approach is first to convert the 3-$(C_1-C_6)$-alkylxanthine in aqueous phase into the corresponding salt using an alkali metal hydroxide and/or alkali metal carbonate, such as, for example, sodium hydroxide, potassium hydroxide, sodium hydrogen carbonate, potassium hydrogen carbonate, sodium carbonate or potassium carbonate. 100 to 120 mol of the abovementioned alkali metal hydroxides or alkali metal carbonates are preferably used per 100 mol of 3-alkylxanthine.

Subsequently a quaternary ammonium or phosphonium compound of the formula III or IV is added in process step b) to the solution or suspension of the 3-alkylxanthine salt. Mixtures of ammonium and/or phosphonium compounds may also be used. The compounds of the formula III and/or IV are either insoluble or only sparingly soluble in water. For this reason, a two-phase mixture is formed, which is composed of the aqueous phase and the phase which is formed by the ammonium and/or phosphonium compounds of the formulae III and IV. The term two-phase mixture is understood to mean the mixture of two liquid phases: a water phase and the phase which contains the ammonium and/or phosphonium compounds of the formulae III and IV. As a rule the two-phase mixture does not contain any further solid/liquid phase boundary. It can, however, come about that flocculation occurs at low temperatures and high concentrations of the xanthine salts. The two-phase mixture is stirred and mixed according to customary methods so that good dispersal of the phases is ensured. 5 to 100 mol of the compounds of the formulae III and/or IV, preferably 10 to 60 mol, in particular 10 to 50 mol, are preferably used per 100 mol of 3-alkylxanthine of the formula II.

Where appropriate, a linear polyether of the formula V may be added to increase the speed of the reaction further. 3 to 100 mol of the linear polyethers of the formula V, preferably 5 to 80 mol, in particular 10 to 50 mol, are preferably used per 100 mol of 3-alkylxanthine of the formula II.

Additionally, an organic solvent, such as, for example, heptane, cyclohexane, dimethylcyclohexane, butyl acetate, amyl acetate, dioxane, anisole or amyl alcohol, can be added to the compounds of the formulae III, IV and V in order to improve the separation of the two-phase mixture of the abovementioned reaction mixture. Preferably, however, no additional solvent is used.

It is advantageous for the added solvent to be insoluble or only sparingly soluble in water. The quantities employed of the solvents may vary over a wide range and can easily be established by a person skilled in the art.

Subsequently, the alkylating agent is added. 102 to 150 mol of methyl chloride, in particular 105 to 140 mol, preferably 108 to 120 mol, or 102 to 150 mol of dimethyl sulfate, in particular 105 to 130 mol, preferably 110 to 120 mol, are required for the methylation of 100 mol, for example, of 3-methylxanthine.

The reaction temperature may vary over a wide range. It is generally —10° to +140° C., preferably from 40° to 110° C. In the alkylation process using methyl chloride, an excess pressure of at most 5 bar is attained in the reaction vessel, so that the reaction can be carried out using equipment which is customary for chemical reactions.

The time for the reaction is generally between 1 hour and 4 hours.

In the alkylation reaction using dimethyl sulfate, the methylsulfuric acid which forms during the reaction is neutralized by the slow addition of alkali metal hydroxide, alkali metal carbonate, alkaline earth metal hydroxide or alkaline earth metal carbonate.

After the time for the reaction has expired, the phases of the two-phase mixture are separated from each other. Then alkali metal hydroxide and/or alkaline earth metal hydroxide and/or alkali metal carbonate is initially added to the 3,7-dialkylxanthine of the formula I, which has flocculated out, until an emulsion is formed. For this purpose, about 80 to 120 mol are as a rule required for the batch size described above.

The phases of the two-phase mixture are now separated from each other according to customary methods. The organic phase, in which the compounds of the formula III and/or IV, as well as, where appropriate, the compound of the formula V, are mainly present, may be employed again for an alkylation reaction, either directly or after washing with water. The aqueous phase, which now contains the 3,7-dialkylxanthine salt and the impurities, is mixed with filtration aids which are based on cellulose or silica, or with active charcoal, and filtered. The filtrate is heated and a mineral acid is quickly added until the pH is favorable for removing the byproducts, at which point the pure 3,7-dialkylxanthine is precipitated. Examples of mineral acids which may be mentioned are: hydrochloric acid, sulfuric acid or nitric acid. Carbonic acid may also be employed.

The temperature at which the precipitation takes place is generally about 50° to 110° C., in particular 75° to 105° C., preferably 85° to 95° C. After the precipitation, the pH of the solution is generally 7 to 10.

The quantity of mineral acid needed is generally 88 to 110 mol.

The solid is subsequently isolated by filtration with suction and washed with water in order to remove byproducts.

The process according to the invention is now illustrated in more detail by the following examples.

EXAMPLE 1

2000 ml of water, 400 g of 3-methylxanthine, 310 g of 33% strength sodium hydroxide solution, 20 g of sodium bicarbonate and 200 g of methyltrioctylammonium chloride are introduced into a reactor. Once the reactor has been tightly sealed, 135 g of methyl chloride are passed in at about 50° C. Subsequently, the reaction is allowed to continue at about 110° C. until there is no further fall in the internal pressure. The reactor is cooled to about 60° C. and briefly evacuated. 310 g of 33% strength sodium hydroxide solution are then added and the organic phase is subsequently separated off. This is then washed with 100 ml of water. The methyltrioctylammonium chloride recovered in this way may be employed again for the next methylation. Active charcoal is added to the aqueous phase and the solution is filtered. Subsequently, the theobromine is precipitated at 85° to 95° C. by dropwise addition of a total of 252 g of 37% strength hydrochloric acid. After cooling, the theobromine is filtered off with suction and then washed with water. After drying to constant weight, 367 g of theobromine are obtained with a content of 99.5% (HPLC); melting point 350.5° to 351° C. This amounts to 84.5% of the theoretical value, based on the starting product 3-methylxanthine.

HPLC determination

Sample preparation 50 mg of theobromine (sample) are suspended in 90 ml of water, and 1 ml of 1M sodium hydroxide solution is added and the sample is dissolved to produce a clear solution. Then the sample is acidified with 2 ml of 1M acetic acid and the solution is made up to 100 ml in a volumetric flask with water. Solutions for comparison: 1 mg of caffeine, 3-methylxanthine and theophylline are dissolved as described above.

Analysis conditions

Quantity injected: 10 μl

Column: RP 8, 250 –4, 10 μm ®Lichrosorb (from E. Merck, Darmstadt),

Flow rate: 1 ml/min

Mobile phase: 80% by volume of 0.1% strength $KH_2PO_4$ solution 20% by volume of methanol Detection: UV detector 273 nm Running time: 20 min Retention time: 3-methylxanthine 4.05 min, theobromine 5.47 min, caffeine 11.15 min Melting point determination The melting points were determined by differential thermal analysis using the Mettler TA3000 system.

EXAMPLE 2

2000 ml of water, 400 g of 3-methylxanthine, 310 g of 33% strength sodium hydroxide solution, 20 g of sodium bicarbonate and 200 g of methyltrioctylammonium chloride and 100 g of diethylene glycol dibutyl ether are introduced into a reactor. Once the reactor has been tightly sealed, 134 g of methyl chloride are passed in at about 50° C. Subsequently, the reaction is allowed to continue at about 90° C. until there is no further fall in the internal pressure. The reactor is cooled to about 50° C. and briefly evacuated. 310 g of 33% strength sodium hydroxide solution are then added and the organic phase is subsequently separated off. This is then washed with 100 ml of water. The methyltrioctylammonium chloride and diethylene glycol dibutyl ether recovered in this manner may be employed again for the next methylation. Active charcoal is added to the aqueous phase and the solution is filtered. Subsequently, the theobromine is precipitated at 85° to 95° C. by the dropwise addition of a total of about 252 g of 37% strength hydrochloric acid. After cooling, the theobromine is filtered off with suction and then washed with water. After drying to constant weight, 376 g of theobromine are obtained with a content of 99.5% (HPLC). This amounts to 86.5% of the theoretical value, based on the starting product 3-methylxanthine.

EXAMPLE 3

2000 ml of water, 400 g of 3-methylxanthine, 294 g of 33% strength sodium hydroxide solution, 200 g of methyltrioctylammonium chloride and 100 g of triethylene glycol dibutyl ether are introduced into a stirring apparatus. Subsequently, 351 g of dimethyl sulfate are added dropwise at about 50° to 60° C. Toward the end of the addition, 16 g of 33% strength sodium hydroxide solution are additionally added dropwise to the reaction mixture. Subsequently, the reaction is allowed to continue at about 60° C. The mixture is cooled and then 310 g of 33% strength sodium hydroxide solution are added. Subsequently the organic phase is separated off. This is then washed with 100 ml of water. The methyltrioctylammonium chloride and triethylene glycol dibutyl ether recovered in this manner can be employed again for the next methylation. The aqueous phase is mixed with active charcoal and filtered. Subsequently, the theobromine is precipitated at 85° to 95° C. by the dropwise addition of a total of about 250 g of 37% strength hydrochloric acid. After cooling, the theobromine is filtered off with suction and then washed with water. After drying to constant weight, 361 g of theobromine are obtained with a content of 99.5% (HPLC). This amounts to 83.2% of the theoretical value, based on the starting product 3-methylxanthine.

We claim:

1. A process for obtaining 3,7-dialkylxanthines of the Formula I

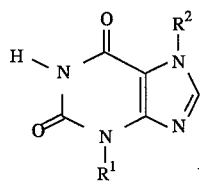

(I)

where $R^1$ and $R^2$, independently of each other, are $(C_1-C_6)$-alkyl, which may be straight-chain or branched, wherein a 3-alkylxanthine of the Formula II

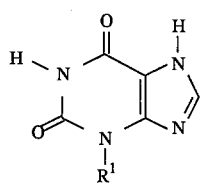

(II)

in which $R^1$ is $(C_1-C_6)$-alkyl, which may be straight-chain or branched, (a) is converted in aqueous phase and using a basic agent into its salt and
(b) this salt is reacted in a two-phase mixture with an alkylating agent with 1 to 6 carbon atoms in the presence of at least one quaternary ammonium compound and/or phosphonium compound of the Formula III or IV

(III)

(IV)

where $R^3$ to $R^{10}$ are identical or different and, independently of each other, are (a) $(C_1-C_{20})$-alkyl, which may be straight-chain or branched,
(b) benzyl or
(c) phenyl and X is an anion.

wherein the alkylation is carried out in the presence of a linear polyether of the Formula V

$R^{11}-O-(Y)_n-R^{12}$ (V)

where $R^{11}$ and $R^{12}$ are identical or different and, independently of each other, are $(C_1-C_8)$-alkyl; Y is a radical from the group (a) $-CH_2-CH_2-O-$ or (b) $-CH_2-CH_2-CH_2-O-$ and n is an integer from 1 to 8.

2. The process of claim 1 wherein 3,7-dialkyl-xanthines of Formula I in which $R^1$ and $R^2$, independently of each other, are $(C_1-C_3)$alkyl, are prepared.

3. The process of claim 2 wherein 3-ethyl-7-propylxanthine or 2-methyl-7-propylxanthine is prepared.

4. The process of claim 1 wherein at least one ammonium compound of the Formula III or phosphonium compound of the Formula IV and polyether of the Formula V is employed, each of which is insoluble or sparingly soluble in water.

5. The process of claim 1 wherein the basic agent is an alkali metal hydroxide, an alkali metal carbonate or a mixture thereof.

6. The process of claim 1 wherein the basic agent is sodium hydroxide, potassium hydroxide, sodium hydrogen carbonate, potassium hydrogen carbonate, sodium carbonate or potassium carbonate; and the quarternary ammonium or phosphonium compound is methyltrioctylammonium chloride, methyltrioctylammonium hydroxide, methyltricaprylammonium chloride, methyltricaprylammonium hydroxide, ethyltrioctylammonium chloride, ethyltrioctylphosphonium chloride or hexadecyltributylphosphonium bromide, and the polyether is ethylene glycoldibutylether, diethylene glycol dibutyl ether, triethylene glycol dibutyl ether, tetraethylene glycol dibutyl ether, diethylene glycol ethyl tert-butyl ether, propylene glycol dibutyl ether, dipropylene glycol dibutyl ether, polyethylene glycol dibutyl ether or polypropylene glycol dibutyl ether.

7. The process of claim 1 wherein the alkylating agent is $(C_1-C_6)$alkylhalide, $(C_1-C_6)$dialkylsulfate or $(C_1-C_6)$dialkylcarbonate.

8. The process of claim 7 wherein the alkylating agent is methyl chloride, ethyl chloride, propyl chloride or dimethyl sulfate.

9. The process of claim 1 wherein 5 to 100 mol of quarternary ammonium or phosphonium compound per 100 mol of 3-alkylxanthine is used.

10. The process of claim 8 wherein 10 to 60 mol of quarternary ammonium or phosphonium compound per 100 ml of 3-alkylxanthine is used.

11. The process of claim 9 wherein 10 to 50 mol of quarternary ammonium or phosphonium compound per 100 mol of 3-alkylxanthine is used.

12. The process of claim 1 wherein the alkylation is carried out at a temperature of −10° C. to 140° C.

13. The process of claim 11 wherein the temperature is from 40° C. to 110° C.

14. The process of claim 1 wherein the molar ratio of 3-alkylxanthine to alkylating agent is 1:1.02 to 1.5.

15. The process of claim 13 wherein the ratio is 1:1.08 to 1.2.

16. The process of claim 1 wherein the quarternary ammonium or phosphonium compound and the polyether have been recycled from a prior reaction of the process.

* * * * *